(12) United States Patent
Mohiuddin et al.

(10) Patent No.: US 11,430,575 B2
(45) Date of Patent: Aug. 30, 2022

(54) SYSTEMS AND METHODS FOR A DATA DRIVEN DISEASE TEST RESULT PREDICTION

(71) Applicant: Specialty Diagnostic (SDI) Laboratories, Inc., Garden Grove, CA (US)

(72) Inventors: Ozman Mohiuddin, Redmond, WA (US); William Henry Haase, Clarksville, TN (US)

(73) Assignee: Specialty Diagnostic (SDI) Laboratories, Inc., Garden Grove, CA (US)

( * ) Notice: Subject to any disclaimer, the term of this patent is extended or adjusted under 35 U.S.C. 154(b) by 0 days.

(21) Appl. No.: 17/097,083

(22) Filed: Nov. 13, 2020

(65) Prior Publication Data

US 2022/0157458 A1 May 19, 2022

(51) Int. Cl.
*G16H 50/20* (2018.01)
*G16H 50/80* (2018.01)
*G16H 10/60* (2018.01)
*G16H 50/30* (2018.01)

(52) U.S. Cl.
CPC .............. *G16H 50/20* (2018.01); *G16H 10/60* (2018.01); *G16H 50/30* (2018.01); *G16H 50/80* (2018.01)

(58) Field of Classification Search
CPC ........ G16H 50/20; G16H 10/60; G16H 50/30; G16H 50/80
USPC ..................................... 702/19; 705/2, 3, 19
See application file for complete search history.

(56) References Cited

U.S. PATENT DOCUMENTS

| 5,366,896 | A  | 11/1994 | Margrey et al. |
| 5,968,731 | A  | 10/1999 | Layne et al. |
| 6,702,988 | B1 | 3/2004  | Sagona et al. |
| 7,666,355 | B2 | 2/2010  | Alavie et al. |
| 8,107,693 | B2 | 1/2012  | Osborne et al. |
| 8,234,129 | B2 | 7/2012  | Michon et al. |

(Continued)

FOREIGN PATENT DOCUMENTS

| WO | WO2017143182 | 8/2017 |
| WO | WO2019102282 | 5/2019 |

OTHER PUBLICATIONS https://fpf.org/2020/05/07/artificial-intelligence-and-the-covid-19-pandemic/.

*Primary Examiner* — Michael Tomaszewski
*Assistant Examiner* — Rachael Sojin Stone
(74) *Attorney, Agent, or Firm* — Caldwell Intellectual Property Law

(57) ABSTRACT

A system for a data driven disease test result prediction, the system comprising a computing device configured to receive user data, wherein the user data includes user parameters, generate, using the user data, training data wherein the training data includes a plurality of entries wherein each entry correlates user parameter data to at least a prediction parameter of the plurality of prediction parameters associated with an infectious disease, train, using the training data and a machine-learning process, a machine-learning model, wherein the trained machine-learning model is configured to generate a plurality of infectivity parameters; compare the plurality of infectivity parameters to a retest target threshold, and determine, as a function of the comparison, a confidence metric, wherein the confidence metric informs a testing protocol.

20 Claims, 8 Drawing Sheets

(56) References Cited

U.S. PATENT DOCUMENTS

| | | | |
|---|---|---|---|
| 8,357,538 B2 | 1/2013 | Self et al. | |
| 8,862,448 B2 | 10/2014 | Holmes et al. | |
| 9,958,466 B2 | 5/2018 | Dalbert et al. | |
| 10,088,460 B2 | 10/2018 | DeWitte et al. | |
| 10,283,217 B2 | 5/2019 | Lui et al. | |
| 11,195,595 B2 * | 12/2021 | Ghiassian | G01N 33/6863 |
| 2008/0091471 A1 * | 4/2008 | Michon | G16H 50/70 |
| | | | 705/3 |
| 2010/0324936 A1 * | 12/2010 | Vishnubhatla | G16H 50/70 |
| | | | 705/3 |
| 2016/0125158 A1 * | 5/2016 | Erdmann | G16H 10/60 |
| | | | 705/3 |
| 2018/0214088 A1 * | 8/2018 | Newberry | A61B 5/6817 |
| 2018/0286497 A1 | 10/2018 | Bauer et al. | |
| 2020/0013488 A1 * | 1/2020 | Lui | C12Q 1/70 |
| 2020/0081023 A1 | 3/2020 | Holmes et al. | |
| 2020/0124868 A1 | 4/2020 | Carrascal De Las Heras et al. | |
| 2020/0388347 A1 * | 12/2020 | Eden | G16H 50/50 |
| 2021/0050116 A1 * | 2/2021 | Sabeti | G06Q 50/01 |
| 2021/0248268 A1 * | 8/2021 | Ardhanari | G06F 21/602 |

\* cited by examiner

SYSTEMS AND METHODS FOR A DATA DRIVEN DISEASE TEST RESULT PREDICTION

FIELD OF THE INVENTION

The present invention generally relates to the field of machine-learning. In particular, the present invention is directed to systems and methods for a data driven disease test result prediction.

BACKGROUND

Coronaviruses are an emerging pandemic threat due to ease of infectivity, low population innate immunity, and asymptomatic spread. Infection typically results in mild respiratory symptoms but can be more serious in infants and older adults, especially those with underlying comorbidities. Respiratory infection is second only to malaria as a cause of infant death worldwide and accounts for substantial hospitalization burden in both age groups in developed countries. Moreover, some pathogens, such as newly emergent zoonotic viral strains, can pose a significant risk of death to the general population as well. Despite intensive social distancing efforts, hand washing, and proper protective equipment, a safe, effective, and routine testing platform is still an elusive goal.

SUMMARY OF THE DISCLOSURE

In an aspect, a system for a data driven disease test result prediction, the system comprising a computing device configured to receive user data, wherein the user data includes user parameters, generate, using the user data, training data wherein the training data includes a plurality of entries wherein each entry correlates user parameter data to at least a prediction parameter of the plurality of prediction parameters associated with an infectious disease, train, using the training data and a machine-learning process, a machine-learning model, wherein the trained machine-learning model is configured to generate a plurality of infectivity parameters, compare the plurality of infectivity parameters to a retest target threshold, and determine, as a function of the comparison, a confidence metric, wherein the confidence metric informs a testing protocol.

In another aspect, a method for a data driven disease test result prediction, the method comprising receiving, by a computing device, user data, wherein the user data includes user parameters, generating, by the computing device and using the user data, training data wherein the training data includes a plurality of entries wherein each entry correlates user parameter data to at least a prediction parameter of the plurality of prediction parameters associated with an infectious disease, training, by the computing device, the training data and a machine-learning process, a machine-learning model, wherein the trained machine-learning model is configured to generate a plurality of infectivity parameters, comparing, by the computing device, the plurality of infectivity parameters to a retest target threshold, and determining, by the computing device, as a function of the comparison, a confidence metric, wherein the confidence metric informs a testing protocol.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for a data driven disease test result prediction. In an embodiment, the system includes a computing device configured to receive user data, which includes a plurality of user parameters including symptomology, age, and user location. Computing device is configured to generate machine-learning training data to generate a trained machine-learning model that correlates user parameters in the training data to prediction parameters associated with an infectious disease, such as Coronavirus (COVID19). The trained machine-learning model is configured to generate a plurality of infectivity parameters. The parameters may include likelihood parameters, severity parameters, and prevalence parameters, together describing various epidemiological factors involved in testing for and mitigating disease. The system may be configured to receive testing protocol data from a user, use a machine-learning process with the trained machine-learning model to generate infectivity parameters for the user, and compare the infectivity parameters to a retest target threshold. Depending on the confidence metric resulting from the retest target threshold, the system may determine a confidence metric and use the metric to inform a testing protocol for the user.

Figure 1:
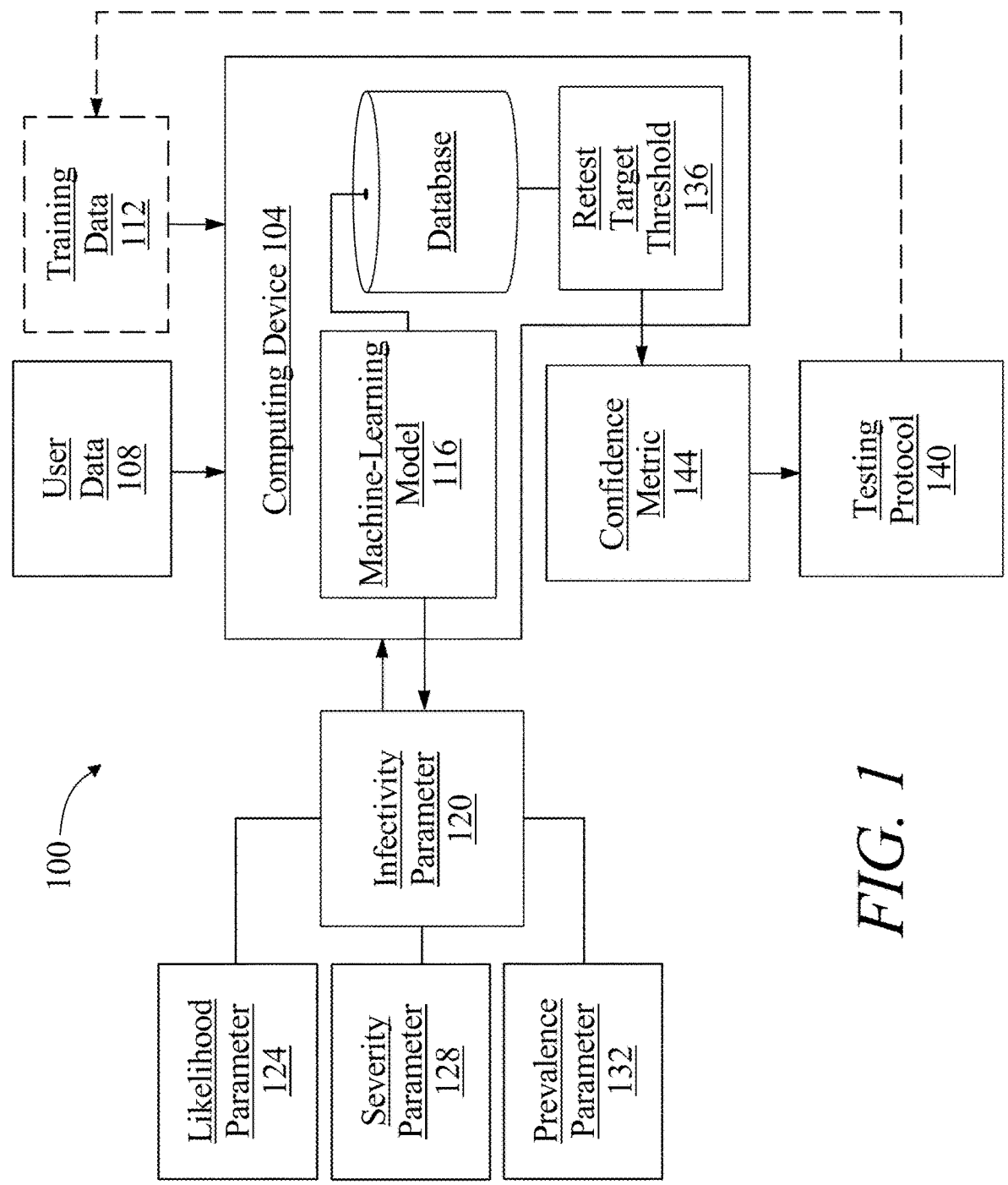
FIG. 1 is a block diagram illustrating an exemplary embodiment of a system of a data driven test result prediction algorithm for infectious disease.

Referring now to FIG. 1, an exemplary embodiment of a system 100 for a data driven test result prediction algorithm for infectious disease is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device 104 is configured to receive user data 108, including at least a user parameters. As used in this disclosure, "user parameters," are elements of data that describe a user's symptomology regarding an infectious disease, a user's age, and a user's geographical location. As used in this disclosure, "user data," includes at least a user parameter and may include additional information germane to infectious disease including user testing protocol data, medical history, physiological data, biochemical data including blood panel data, presence of antibodies, and the like. As used in this disclosure, "testing protocol data," is data regarding a type of diagnostic procedure a user may have taken, such as a reverse transcription polymerase chain reaction (RT-PCR) test, an antigen test, antibody test, bacterial culture, enzyme-linked immunosorbent assay (ELISA), or any other diagnostic procedure associated with testing for an infectious disease, and may include a testing date, location and/or a result. Testing protocol data may include a user's status regarding having taken an antigen test, or data regarding the outcome of the antigen test, the date the test was taken, the location of submitting the test, the testing provider, etc. As used in this disclosure, "infectious disease," is any disease wherein the etiological agent(s) is caused by an organism or organismal product—such as a bacteria, virus, fungi, parasite, spore, etc. Infectious diseases may be spread human-to-human, from a common reservoir such as a particular habitat, animal, body of water, and the like. Infectious diseases may be spread by a vector, such as blood-feeding arthropods including mosquitoes, ticks, and fleas. Persons skilled in the art, upon review of this disclosure in its entirety, will be aware how the data driven test result prediction algorithm for infectious disease may be applicable to and useful for a variety of user data for a variety of infectious diseases.

Continuing in reference to FIG. 1, the infectious disease may include a coronavirus such as the 2019-novel Coronavirus acute respiratory disease (COVID-19), as caused by Severe Acute Respiratory Syndrome Coronavirus 2 (SARS-CoV-2) virus strain. The SARS-CoV-2 virus strain, which is the etiological agent of the COVID-19 disease, is a member of the Coronaviridae family of enveloped, positive-strand RNA viruses which infect a variety of amphibians, birds, and mammals. There are several clades of coronaviruses which infect humans, such as Severe Acute Respiratory Syndrome virus (SARS) and Middle Eastern Respiratory Syndrome virus (MERS). The system 100 for a data driven test result prediction algorithm for infectious disease may be used for a plurality of infectious diseases but may be described in illustrative embodiments with SARS-CoV-2 and COVID-19.

Continuing in reference to FIG. 1, computing device 104 is configured to generate, using the user data 108, training data, which may have any form suitable for training data as described in further detail below. Training data includes a plurality of entries wherein each entry correlates user parameter data to at least a prediction parameter of the plurality of prediction parameters associated with an infectious disease. A "prediction parameter," as used in this disclosure, is a qualitative and/or quantitative score, metric, value and/or mathematical expression used for quantifying, enumerating, or otherwise describing, parameters associated with an infectious disease. For instance and without limitation, a prediction parameter may include a numerical value range for assigning the likelihood of COVID-19 according to clinical manifestation; such as a score of 0-100 wherein the prediction parameter identifies the symptoms that resemble infection and those that do not. For instance, a sore throat or runny nose may represent a numerical value of '5', but a dry cough may be a '30'. In such an example a user exhibiting a 'dry cough', 'chest pain', 'chills', and 'fatigue' may have prediction parameters associated with a numerical value for each symptom and a mathematical expression for combining the scores associated with the plurality of symptoms, such as a summation of the series of scores. This may be done to determine what 'score' or 'value' each symptom should have assigned to it. Prediction parameters determined from training data may include educated bifurcations of data as it relates to the infectious agent, such as age cutoffs for determining risk scores associated with "likelihood" and "severity" of disease. For example, prediction parameters for COVID-19 regarding age may have higher numerical values for children under 5 and individuals over 65 but may have lower-than-standard numerical values associated with individuals who are from adolescence through teens, whereas standard values may apply to individuals from 25-48 years of age. The age cutoffs and the numerical values assigned may be examples of prediction parameters that are derived from the training data, for instance for COVID-19.

Continuing in reference to FIG. 1, "training data," as used in this disclosure, is data regarding user data 108 that may be used for training a machine-learning model. Training data 112 may include a plurality of user data 108 from a plurality of users, for instance from a range of ages, a variety of symptoms, several different locations, and different positive/negative test outcomes for a plurality of test types. Training data 112 may be obtained directly from users, for instance via a questionnaire, mobile application portal, web-based inputs, and the like. Training data 112 may originate from online research and/or data repositories such as the National Institutes of Health (NIH), Center for Disease Control (CDC), and the like.

Continuing in reference to FIG. 1, training data 112 may include data containing correlations that a machine-learning process may use to model relationships between two or more categories of data elements. For instance, and without limitation, training data 112 may include a plurality of data entries, each entry representing a set of data elements that were recorded, received, and/or generated together; data elements may be correlated by shared existence in a given data entry, by proximity in a given data entry, or the like. Multiple data entries in such training data 112 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 112 according to various correlations; correlations may indicate causative and/or predictive links between categories of data elements, which may be modeled as relationships such as mathematical relationships by machine-learning processes, as described in further detail below. Training data 112 may be formatted and/or organized by categories of data elements, for instance by associating data elements with one or more descriptors corresponding to categories of data elements, for instance categorized by age, symptom, location, test result, test type, and the like. As a non-limiting example, training data 112 may include data entered in standardized forms by persons or processes, such that entry of a given data element in a given field in a form may be mapped to one or more descriptors of categories. Elements in training data 112 may be linked to descriptors of categories by tags, tokens, or other data elements; for instance, and without limitation, training data 112 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data, as described for use in machine-learning processes in further detail below.

Continuing in reference to FIG. 1, generating training data 112 may include receiving a parameter category and generating training data 112 as a function of the parameter category. A "parameter category," as used in this disclosure, is a category of users, which may share some characteristic and/or data. A parameter category may include classification, as described in further detail below. A parameter category may include a user category for generating training data 112 as a function of the user category. A "user category," as used in this disclosure, is a categorization of a data type as a it relates to user data, and a plurality of data that belongs to the category. A user category that may be used to generate training data may include a list of COVID-19 patients who have tested positive using an antigen test, wherein the list contains a plurality of user ages and symptoms. In such an example, computing device 104 may generate training data 112 after receiving the user categories of "age" and "symptom" and "test result". Computing device 104 may format data, as described above, for instance as .csv formatted data wherein columns are linked to a user category type. Elements in a column may be linked to other elements, for instance each user's age is related to that user's location and symptoms. Correspondingly, elements may not be linked, and each user category used separately as training data 112. Training data 112 may be received directly as a user category.

Continuing in reference to FIG. 1, computing device 104 is configured to train, using the training data 112 and a machine-learning process, a machine-learning model, wherein the trained machine-learning model is configured to generate a plurality of infectivity parameters. Computing device 104 may train a machine-learning model, such as a classification machine-learning model, clustering machine-learning model, among other models, with training data 112 that corresponds to elements of user data 108. A machine-learning model 116 may include any machine-learning algorithm, process, or the like, as described in further detail below. Correspondingly, a machine-learning process may be any machine-learning algorithm performed by a machine-learning module, as described in further detail below. Training the machine-learning model 116 to generate a plurality of infectivity parameters as a function of the training data 112 may include training the machine-learning model 116 as a function of user data 108 that includes a plurality of entries wherein each entry models user parameters to data related to prediction parameters associated with an infectious disease, such as COVID-19. Machine-learning model 116 may be generated by using a machine-learning algorithm to train a machine-learning model as a function of training data 112 that includes user data 108, wherein the training data 112 is categorized in a variety of ways. A machine-learning model 116 trained in such a way may generate outputs that include disease-specific prediction parameters, including age ranges for susceptibility to the disease, identified symptomology relevance, location "hotspots", among other useful determinations, correlations, functions, and/or relationships. With increasing volume of user data 108, computing device 104 may generate larger training data 112 sets for training the machine-learning model 116, which may result in more robust prediction parameters and more accurate infectivity parameters.

Continuing in reference to FIG. 1, "infectivity parameters," as used in this disclosure, are a set of measurable factors describing the likelihood an individual has a particular infectious disease, the severity of the infectious disease in the user, and the prevalence of the infectious disease in a particular location. Infectivity parameters 120 may include a likelihood parameter, a severity parameter, and a prevalence parameter. Computing device 104 may accept an input of user parameters and, using the trained machine-learning model 116, output a plurality of infectivity parameters 120. Infectivity parameters 120 may include other parameters including parameters describing rates of infection in a population, for instance the instantaneous change in positive case rate for a zip code.

Continuing in reference to FIG. 1, the plurality of infectivity parameters 120 may include a likelihood parameter. A "likelihood parameter," as used in this disclosure, is a quantitative measure of the likelihood that the symptomology data observed for the age of the user is associated with a particular infectious disease. The likelihood parameter 124 may include a numerical value and/or a series of numerical values described as a function. For instance, the likelihood parameter 124 may include a mathematical expression of numerical values such as a value for the user's age, a value for each symptom, and a value for the prevalence of the disease at the user's zip code, wherein the mathematical expression uses addition, multiplication and division to provide a single numerical value which is the likelihood parameter 124 describing the likelihood that the user is experiencing a particular infectious disease. A likelihood parameter 124 may include a vector, wherein the axial components are the values assigned for user's age and symptoms, wherein the magnitude of the vector components are derived as a function of the machine-learning model 116 and the training data 112, and the vector itself describes the likelihood, or propensity, for an infectious disease. Likelihood parameter 124 may include a matrix, wherein the matrix represents a system of equations and each row of the matrix contains coefficients from the equations describing the user's age, symptoms, among other factors. In such an example, then matrix may contain a plurality of numerical values arranged in a 2D array and may follow the rules of linear algebra that may be solved for a singular value, or several values, that represent the likelihood parameter 124. In non-limiting illustrative examples, a user of 70 years of age, experiencing 'shortness of breath', 'dry cough', and 'fatigue' may have a numerical value associated with each on a scale of 0-30, with the summation of the numerical values on a scale of 0-100 indicating the likelihood of suffering from COVID-19. In such an example, the user may have a likelihood parameter 124 of a singular numerical value of '91' indicating a very high likelihood, or probability, the user is experiencing COVID-19. In such an example, the user may be directed to receive a diagnostic procedure for determining the status of infection, such as an antigen test and/or a RT-PCR test. Additionally, given a prevalence of infection for the user's location, including all recent locations a user may have been, a more robust likelihood parameter 124 may be determined.

Continuing in reference to FIG. 1, the plurality of infectivity parameters 120 may include a severity parameter. A "severity parameter," as used in this disclosure, is a quantitative measure of the severity of the particular infectious disease as a function of age and symptomology. The severity parameter 128 may include a numerical value and/or a series of numerical values described as a function. For instance the severity parameter 128 may include a mathematical expression of numerical values for instance a value for the user's age, a value for each symptom, and a value for the prevalence of the disease at the user's zip code, wherein the mathematical expression uses addition, multiplication and division to provide a single numerical value which is the severity parameter 128 describing the severity of the particular infectious disease the user may be experiencing. A severity parameter 128 may include a vector, wherein the axial components are the values assigned for the user's age and symptoms, wherein the magnitude of the vector components are derived as a function of the machine-learning model 116 and the training data 112, and the vector itself describes the severity, or clinical progression, of an infectious disease. Severity parameter 128 may include a matrix, wherein the matrix represents a system of equations and each row of the matrix contains coefficients from the equations describing the user's age, symptoms, among other factors. In such an example, then matrix may contain a plurality of numerical values arranged in a 2D array and may follow the rules of linear algebra that may be solved for a singular value, or several values, that represent the severity parameter 128.

Continuing in reference to FIG. 1 the plurality of infectivity parameters 120 may include a prevalence parameter. A "prevalence parameter," as used in this disclosure, is determined as a function of the incidence of the infectious disease at the user location and described the prevalence of an infectious disease, including prevalence rate, number of positive cases, and the like. The incidence of the infectious disease at the user location may be represented as the number of positive tests (number of cases) per geographical location, such as a zip code, city/town, county, state, country, and the like. The incidence of the infectious disease at the user location may be represented as the number of positive tests per capita in a region. The prevalence parameter 132 may include a numerical value and/or a series of numerical values described as a function. The prevalence parameter 132 may include, and/or be calculated by, a mathematical expression of numerical values for instance a value(s) for the likelihood and severity for a single user and/or plurality of users, and a value for the prevalence of the disease at a first user's zip code, wherein the mathematical expression uses addition, multiplication and division to provide a single numerical value which is the prevalence parameter 132 describing the prevalence of the particular infectious disease at the first user's location. The incidence of the infectious disease may include the number of cases in a region as a function of time. In this case, the prevalence may be, for instance, an instantaneous rate of a function describing the number of cases in a defined area over time, wherein the prevalence is a slope of the function at a particular point in time. A prevalence parameter 132 may include a vector, wherein the axial components are the total number of cases and the rate of positive tests for a region, wherein the magnitude of the vector components are derived as a function of the machine-learning model 116 and the training data 112, and the vector itself describes the prevalence parameter 132. The prevalence parameter 132 may include the likelihood a user will encounter an infected individual in a region. Prevalence parameter 132 may include a matrix, wherein the matrix represents a system of equations and each row of the matrix contains coefficients from the equations describing the number of positive tests, type of test, false positive/false negative rate, among other factors. In such an example, then matrix may contain a plurality of numerical values arranged in a 2D array and may follow the rules of linear algebra that may be solved for a singular value, or several values, that represent the prevalence parameter 132.

Continuing in reference to FIG. 1, infectivity parameters 120 may be represented, for instance and without limitation, as polar coordinates (2D/3D geometric analysis, discrete areas inform metric), vector analysis, scatter plots, box graphs, population percentile, mean, standard deviation, among other statistical and mathematical parameters. Infectivity parameters 120 for each user may be expressed as 3-Dimensional (3D) coordinates, such as (x, y, z) coordinates where points may include numerical values represented in a 3-Dimensional (3D) coordinate space, such as a Cartesian coordinate system, wherein the coordinates inform parameters in 3D. For instance, each 3D coordinate may be a determination of the machine-learning model 116, machine-learning process, and/or algorithm that accepts directly observable data (user parameters) in through training data 112 to determine the (x, y, z) coordinates, wherein each coordinate may include directly-observable and/or directly-unobservable parameters. Directly unobservable parameters may represent parameters that were not directly present in the training data 112, such as the prevalence of disease for the user's zip code but may be revealed from a machine-learning determination, provided a large degree of data for that zip code is obtained. For instance and without limitation, training data 112 may relates age and symptoms (observed as training data inputs) to likelihood and severity (unobserved; determined from the observed inputs), wherein the probability a user has a particular infectious disease and it's seriousness were not directly observable from inputs, the machine-learning model 116 may be trained with such data over discrete time periods (first day, one week post positive test, etc.) and relate a user's lifestyle, sex, age, overall health, location, etc. to normal thresholds (such as prediction parameters) to determine which infectious disease, its spread (prevalence), time course of disease, rates of infection, etc. In such a case, likelihood and severity values may represent parameters (coordinates) such as an (x, y) pair; the values for the likelihood parameter 124, severity parameter 128, and Continuing in reference to FIG. 1, infectivity parameters 120 may be represented, for instance and without limitation, as normalized scales such as percentile ranges, for instance shown in a separate graphical user interface (GUI) panel, page, or the like, by scatter plots, box plots, or the like, wherein a range of values for a parameter are shown with statistical values that relate to the full range of values expected for a population. Infectivity parameters 120 may be represented in this manner as a function of the plurality of prediction parameters the training data 112 entries are correlated to. In such a case, the range of values may include being represented along a 1-Dimensional graphical display, such as a number line, and the range of values constitutes the full spectrum for the population of that parameter/metric. Such a population may be recognized by a classifier from a classification machine-learning process. In using a classification machine-learning process, a classifier may be determined based on a subset of alike users, for instance, sharing common characteristics relating to age, sex, fitness level, socioeconomic status, disease state, location, testing protocol, and the like. Larger datasets will provide more robust scales, wherein a classification machine-learning process may access a web-based research database, online data repository, NOSQL database, text-based online query methodology, and the like.

Continuing in reference to FIG. 1, training the machine-learning model 116 using the machine-learning process may include generating a numerical value scale for the plurality of infectivity parameters 120 as a function of the training data 112, and outputting, using the trained machine-learning model 116, the user data 108 input, and the numerical value scale, a quantitative value for each parameter of the plurality of infectivity parameters 120. A "numerical value scale," as used in this disclosure, is a range of quantitative values on which a parameter can be identified as having a specific quantitative value. For instance, and without limitation, a numerical value scale may include all whole numbers [0, 1000], all integers [−100, 100], and the like, along which each parameter may be placed and provided a value. The trained machine-learning model may be used to generate numerical value scales for quantifying the likelihood parameter 124, severity parameter 128, and/or prevalence parameters 132, including the range of the scale and how a particular value for one parameter relates to another. For instance, computing device 104 may determine an appropriate level of numerical value (or scoring) that should be assigned to a user for "likelihood of having COVID-19" according to the manifestation of symptoms such as 'dry cough' or a 'fever', the age of the user, and the location of the user. In such an example, the machine-learning process and trained machine-learning model 116 may determine, from the training data 112, the presence of certain symptoms, such as 'fever', 'dry cough', and 'shortness of breath', are highly correlated with COVID-19, and a combination of these symptoms should be set to a nominal score of '100', wherein 'fever', 'dry cough', and 'shortness of breath' receive higher numerical values than other symptoms, but in combination, receive an even higher score than simple addition would imply, due to the increased likelihood experiencing all of those symptoms may have for COVID-19. The numerical value scale for the likelihood parameter 124 may differ from user location to user location. Likewise, the numerical value scale for severity parameter 128 may differ from user to user as a function of age, where the same symptoms shared between two users that differ in age may be given different severity parameters 128. In such an example, the user age may be a coefficient, variable, or additive factor used in calculating the numerical value, or determining the scale from which the value is obtained. The machine-learning process and trained machine-learning model 116 may determine appropriate numerical values for each parameter depending on the trends, patterns, and heuristics observed in the training data 116. Alternatively, or additionally, the numerical value scale of one parameter may be influenced by another. For instance and without limitation, higher prevalence parameter 132 values may change the scaling for scoring likelihood parameters 124 because it may be anticipated that with higher concentration of cases, the likelihood of a particular clinical manifestation in accordance with COVID-19 would increase the likelihood a user is in fact infected.

Continuing in reference to FIG. 1, computing device 104 is configured to compare the plurality of infectivity parameters 120 to a retest target threshold. Computing device 104 may first rank (or weight), using a ranking function, the plurality of infectivity parameters 120 and compare the plurality of ranked infectivity parameters 120 to the retest target threshold. A "retest target threshold," as used in this disclosure, is a value, which if exceeded by an infectivity parameter 120, or infectivity parameter aggregate, may indicate a user should undergo a particular testing protocol 140, for instance be tested and/or retested for COVID. A retest target threshold 136 may include a numerical value, a percentile, percentage, or any other mathematical quantifier for comparison of the infectivity parameters 120. A "testing protocol," as used in this disclosure, is a procedure or system of rules and/or instructions governing the identification of an infectious disease in a user and/or assigning a treatment to the user based on the identification. For instance, a testing protocol 140 for a user thought to have COVID-19 may include an antigen test, or if an antigen test is administered and returns a potential false negative, an RT-PCR test as a second, confirmatory test. A pairwise comparison, such as subtraction, of an aggregation of the plurality of infectivity parameters 120 from the retest target threshold 136 value may indicate an overall likelihood that an individual should be tested, and the likelihood that the test result indicates a true positive and/or negative result, as described in further detail below.

Continuing in reference to FIG. 1, ranking the plurality of infectivity parameters 120 using a ranking function, may include weighting, or otherwise modifying, the infectivity parameters 120. Weighting may include adjusting the infectivity parameters using a weighting factor, or a dimensionless multiplicative factor that may be used to convert infectivity parameters 120 to directly comparable values for comparing to the retest target threshold 136. For instance, the likelihood parameter 124, severity parameter 128, prevalence parameter 132, and/or combinations thereof may be weighted among a standard numerical scale so that users from a wide range of ages, symptoms, and regions can be more easily compared to a standard retest target threshold 136 value to determine testing protocols 140. A ranking function may include a table of values used to weight parameters. A ranking function may be used to adapt to changing priorities, for instance the system 100 may treat likelihood parameters 124 and severity parameters 128 with weights (a and b) that may add up to 100% of a score used control priority of each component. In such an instance, the likelihood parameter 124 multiplied by a, and the severity parameter 128 multiplied by b, may provide a prioritized ranking (weight) of the parameters. In non-limiting illustrative examples, if the likelihood parameter were to be prioritized for determining a testing protocol 140, then with a=0.8 and b=0.2, the aggregate result of the two parameters may be indicated by (likelihood parameter*0.8)+(severity parameter*0.2)=weighted infectivity parameter aggregate.

Continuing in reference to FIG. 1, a ranking function may include an objective function, wherein the objective function may include performing a greedy algorithm process. A "greedy algorithm" is defined as an algorithm that selects locally optimal choices, which may or may not generate a globally optimal solution, and then such a ranking function would then weight the infectivity parameters 120 based upon an optimal priority for each. For instance, computing device 104 may select weights associated therewith that are best for ranking each parameter, wherein the weight relates to, for instance, the numerical impact the parameter has on testing and/or retesting the user for COVID-19. For instance and without limitation, a machine-learning process may use a table of values for weighting parameters and may rank each parameter, and combination thereof, as a function of impact of the parameter on determining the appropriate testing protocol 140.

Continuing in reference to FIG. 1, alternatively or additionally, in non-limiting illustrative examples a ranking function may include a linear objective function, wherein the computing device 104 may solve using a linear program, such as without limitation, a mixed-integer program. A "linear program," as used in this disclosure, is a program that optimizes a linear objective function, given at least a quantifier and/or ranking score based on impact of an infectivity parameter 120, user data 108, and/or prediction parameter; a linear program may be referred to without limitation as a "linear optimization" process and/or algorithm. For instance, in non-limiting illustrative examples, a linear program may use a linear objective function to calculate impact for a level of prevalence in a region for its impact on likelihood of COVID-19 versus another infectious disease. A mathematical solver may be implemented to solve for the set of weighting factors that maximizes impact scores for a particular use; mathematical solver may be implemented on computing device 104 and/or another device in system 100, and/or may be implemented on third-party solver. Computing device 104 may use a linear optimization process to determine which combination of infectivity parameters 120 should be aggregated for comparing to the retest target threshold for obtaining a particular number of users to be retested for COVID.

Continuing in reference to FIG. 1, ranking function may include minimizing a loss function, where a "loss function" is an expression of an output of which a ranking process minimizes to generate an optimal result. As a non-limiting example, computing device 104 may assign variables relating to a set of weights for infectivity parameters 120, which may correspond to impact score components and priority score components, and calculate an output of mathematical expression using the variables, and select an objective that produces an output having the lowest size, according to a given definition of "size," of the set of outputs representing each of plurality of candidate ingredient combinations; size may, for instance, included absolute value, numerical size, or the like. For instance in non-limiting examples, a loss function may rank an optimal set of infectivity parameters 120 based upon how each parameter may reduce the numerical value for users of certain age ranges so that a minimal number of testing is done while maximizing testing of at-risk populations. Selection of different loss functions may result in identification of different potential pairings as generating minimal outputs. Persons skilled in the art, upon reviewing the entirety of this disclosure, will be aware of various embodiments in which a ranking function may take form and be system 100 to rank, or otherwise weight, infectivity parameters 120 based on some criteria as it relates to a retesting threshold value.

Continuing in reference to FIG. 1, the algorithm can be 'tuned' to suit requirements for a particular use by weighting infectivity parameters 120 and/or aggregating infectivity parameters 120. For instance, the algorithm may control the retest target threshold 136 to obtain a particular retest target percentage of users for a particular subset of users, particular region, etc., wherein the values necessary to trigger a particular testing protocol 140 are unique to a set of users or particular region. This may be useful for regions with test shortages or overburdened medical capabilities. This level of adaptability is inherent in the algorithm according to the machine-learning model 116 from the training data 112 used, wherein the infectivity parameter 120 numerical value scales may be adjusted as more user data 108 is obtained or as prevalence increases. For instance, and without limitation, a region with a lower prevalence may have a higher retest target threshold 136 value than a region with a statistically significant increase in prevalence.

Continuing in reference to FIG. 1, system 100 may include using a machine-learning process to combine infectivity parameters 120 for comparing the plurality of ranked infectivity parameters 120 to the retest target threshold 136. Infectivity parameters 120 may be aggregated or otherwise combined into a singular numerical value by using a mathematical expression, for instance using multiplication and addition, as described above with weighted parameters. Infectivity parameters 120 may be omitted for comparing to the retest target threshold 136, for instance only the likelihood parameter 124 and severity parameter 128 may be used. Retest target threshold 136 may be a constant value compared against, for instance above which a particular testing protocol 140 is always returned. Retest target threshold 136 may include a particular numerical value of a parameter as determined by the trained machine-learning model 116 from training data 112 corresponding to user parameters. Retest target threshold 136 may be a fluid variable that is dependent on testing capability, prevalence in a region, among other variables. Computing device 104 may for instance assign a percentile (0-100) for each infectivity parameter 120 and may set the retest target threshold 136 according to the percentile, where users with parameters above for instance $25^{th}$ percentile will trigger an output of a particular testing protocol 140 output.

Continuing in reference to FIG. 1, testing protocol 140 may include a decision-tree model for an infectious disease. For instance, a decision-tree model for infectious disease may include a dichotomous key for determining the identity of an infectious agent, such as is used in diagnosing and treating bacterial infections. A testing protocol 140 may include a decision-tree model that is a decision support tool that uses a tree-like model of decisions and their possible consequences, including chance event outcomes, resource costs, and utility. A decision-tree model is one way to display an algorithm that only contains conditional control statements. A decision tree is a flowchart-like structure in which each internal "root node" represents a "test" on an attribute (e.g. whether an antigen test is a positive or negative), each branch from the root node represents the outcome of the test, and each "leaf node" branched from the root node represents a class label (decision taken after computing all attributes from the outcome of the root node). The paths from root node to leaf node represent classification rules. In non-limiting illustrative examples, a node may represent the testing protocol 140 decision for an antigen test for COVID-19, wherein if negative may trigger the testing protocol 140 decision for a confirmatory RT-PCR test, wherein if positive may trigger a testing protocol 140 for a treatment regimen or course-of-action.

Continuing in reference to FIG. 1, the retest target threshold 136 may be determined as a function of the trained machine-learning model 116 and the numerical value scale for the prevalence parameter 132. The trained machine-learning model 116 may be trained on outcomes from regions where universal (compulsory) testing was adopted at various times points (1 mo. post-epidemic; 3 mo. post-epidemic, etc.) to determine true prevalence parameters 132 and set a retest target threshold 136 based on incidence of COVID-19 cases. The retest target threshold 136 may be further modified by testing capability, at-risk designation based on age, severity parameter 128, among other factors.

The retest target threshold 136 may include being set as a function of a historical distribution of infectivity parameters 120, wherein changes in likelihood parameter 124, severity parameter 128, and/or prevalence parameter 132 may be used to calculate a retest target threshold 136.

Continuing in reference to FIG. 1, computing device is configured to determine, as a function of the comparison, a confidence metric, wherein the confidence metric informs a testing protocol 140. The comparison of the plurality of infectivity parameters 120 (ranked or otherwise) to the retest target threshold 136 may result in a confidence metric to inform a testing protocol 140. A "confidence metric," as used in this disclosure, is a metric describing how an infectivity parameter 120 compares to a retest target threshold 136, wherein the metric is a numerical value describing the confidence in the testing protocol 140 that results from the comparison. A confidence metric 144 may be produced by a machine-learning process and/or machine-learning model. Confidence metric 144 may include a percentage, that if high enough, dictates that a retesting protocol be conducted. In non-limiting illustrative examples, confidence metric 144 may result from subtraction of the plurality of infectivity parameters 120, either individually or in aggregate, from the retest target threshold 136, wherein depending on the value of the confidence metric 144, will trigger a testing protocol 140. In such an example, if the confidence metric 144 indicates a high likelihood the user is infected with COVID-19, but the user data includes a negative antigen test, the testing protocol 140 informed by the confidence metric 144 may include a second, RT-PCR test. Computing device 104 may know which "path" to which "node" of a decision-tree to take depending on the confidence metric 144. A pairwise comparison, such as subtraction, of an aggregation of the plurality of infectivity parameters to the retest target threshold 136 value may indicate a confidence metric 144, wherein the confidence metric 144 can signal i) an overall likelihood that an individual should be tested, and ii) that the likelihood that the test is a true positive and/or negative result. For instance, if the magnitude of the confidence metric 144 is such that there is a high degree of confidence that an individual is COVID-19-positive, then a negative antigen test is likely to represent a false negative test result, and such a confidence metric 144 may inform a testing protocol 140 of a RT-PCR retest for confirmation.

Continuing in reference to FIG. 1, determining the confidence metric 144 may include determining a quantification of a relationship between the retest target threshold 136 and the plurality of infectivity parameters 120 and generating an output to retest a user as a function of the testing protocol 140 and the relationship between the rest target threshold 136 and the plurality of infectivity parameters 120. A quantification of a relationship may include a numerical value, a percentile value such as x % of users at this level of matching retest target threshold 136 test positive, etc. For instance in non-limiting illustrative examples, if comparison of the plurality of infectivity parameters 120 to the retest target threshold 136 indicates the a user should be tested for COVID-19 due to comparison to other users with alike infectivity parameters 120, and the antigen test returns a negative result, the confidence metric 144 may indicate a high percentage value that such a result is a false negative and instruct a testing protocol of a confirmatory RT-PCR test. Confidence metric 144 may capture the relationship of the infectivity parameters 120 to the retest target threshold 136 and indicate if a first, or even second test, is a false positive and/or false negative. Confidence metric 144 may include a numerical value, function of values, matrix, array, vector, or the like, as described above for infectivity parameters 120. Alternatively or additionally, if a user has a low likelihood parameter 124 and low severity parameter 128 due to being 22 years of age and having no symptoms, but returns a positive result from testing, the user may represent an asymptomatic individual. User data 108 from such a user may assist in training the machine-learning model 116 to detect asymptomatic users and/or asymptomatic spread of COVID-19. In such an instance, a prevalence parameter 132 compared to the retest target threshold 136 may indicate a high confidence metric 144 that the user is in fact COVID-19 positive despite having no symptoms.

Figure 2:
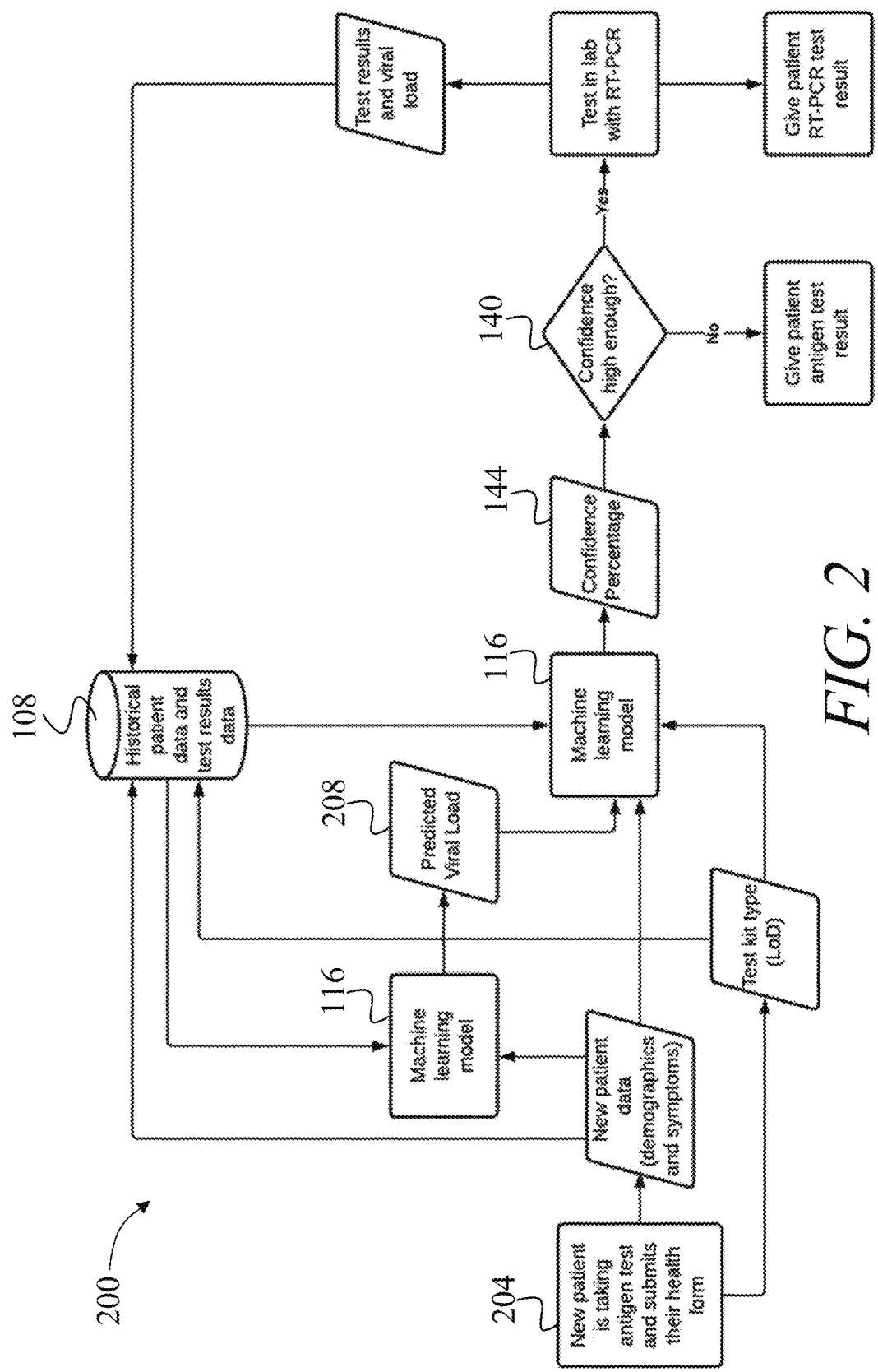
FIG. 2 is a block diagram illustrating an exemplary embodiment of the process flow of the data-drive test prediction algorithm for infectious disease.

Referring now to FIG. 2, an exemplary embodiment 200 of the system 100 may include receiving user testing protocol data, and using the user testing protocol data as an input into the machine-learning process, and determining, using the trained machine-learning model 116, a confidence metric 144 wherein the confidence metric 144 represents a numerical difference between the user testing protocol data and the retest target threshold 136. System 100 may accept an input of a user testing protocol data 204 which may include new user data 108 such as demographics (age and location) and symptoms. Test protocol data 204 may be stored and/or retrieved from a database, as described in further detail below. Machine-learning model 116 may train with training data 116 containing the testing protocol data 204; alternatively or additionally, the trained machine-learning model 116 may be used with the testing protocol data 204 to determine a variety of data. For instance and without limitation, the likelihood parameter 124, severity parameter 128, test result data (and its correspond limit of detection [LoD]), age of user, and time course of infection may be used to determine a predicted viral load 208. The computing device 104 may use a machine-learning process and the trained machine-learning model 116 to determine what a viral load 208 for a user with a particular set of parameters and data may harbor. The viral load 208, or viral burden, may include the viral titer which is a numerical expression of the number of infectious particles the user may harbor and/or be expelling, shedding, or otherwise spreading. The viral load 208 may be determined as the quantity of virus in a given volume of fluid, for instance blood, *salvia*, sputum, and the like. Viral load 208 numerical values may be stored and/or retrieved alongside, or linked to, other elements used as training data 112 for refining and/or retraining machine-learning models 116. Persons skilled in the art may appreciate that viral load 208 may be synonymous with colony forming units per milliliter volume (CFU/mL) which is a standard measurement for viable bacteria in bacterial infections. The system 100 may work similarly with bacterial infectious diseases.

Still referring to FIG. 2, computing device 104 may generate a confidence metric 144, for instance expressed as a percentage, wherein the percentage is a quantification of the relationship between the infectivity parameters 120, test result, time course of infection, viral load 208, among other factors. The confidence metric 144 may inform computing device 104 if the testing protocol data 204 is accurate, for instance if the infectivity parameters 120 may indicate a user has a particularly low viral load 208, but may still be COVID-19 positive, and the antigen test returns a negative result, the confidence metric 144 may dictate that the testing protocol 140 (is confidence high enough?) indicate testing in a lab with RT-PCR as a confirmatory procedure. It is important to note in FIG. 2, that the viral load and limit of detection (LoD) of various tests represent data that may become training data 112, either for machine-learning model 116 and/or for a second machine-learning model.

Figure 3:
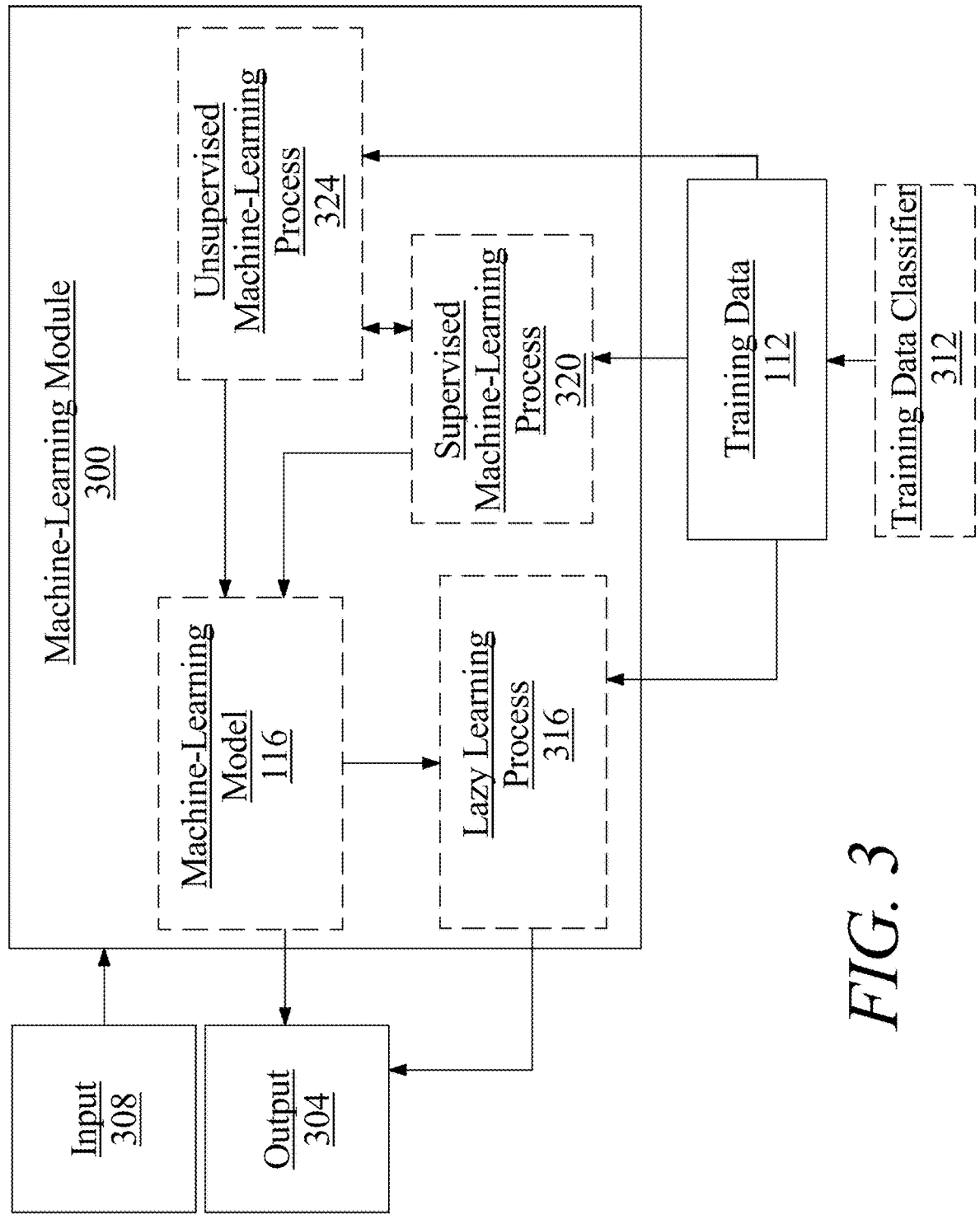
FIG. 3 is a block diagram illustrating an exemplary embodiment of a machine-learning module.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 112, as described above, to generate an algorithm that will be performed by a computing device/module to produce outputs 204 given data provided as inputs 208; this is in contrast to a non-machine learning software program where the commands to be executed are determined in advance by a subject and written in a programming language.

Alternatively or additionally, and continuing to refer to FIG. 3, training data 112 may include one or more elements that are not categorized; that is, training data 112 may not be formatted or contain descriptors for some elements of data. Machine-learning algorithms and/or other processes may sort training data 112 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 112 to be made applicable for two or more distinct machine-learning algorithms as described in further detail herein. Training data 112 used by machine-learning module 300 may correlate any input data as described in this disclosure to any output data as described in this disclosure.

Further referring to FIG. 3, training data 112 may be filtered, sorted, and/or selected using one or more supervised and/or unsupervised machine-learning processes and/or models as described in further detail herein; such models may include without limitation a training data classifier 312. Training data classifier 312 may include a "classifier," which as used in this disclosure is a machine-learning model as defined herein, such as a mathematical model, neural net, or program generated by a machine learning algorithm known as a "classification algorithm," as described in further detail herein, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a process whereby a computing device and/or any module and/or component operating thereon derives a classifier from training data 112. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 312 may classify elements of training data 112 to elements that characterizes a sub-population, such as a subset of user parameters including age, symptoms, zip codes, city/town, test results, COVID-19 statuses, contract tracing data, and/or phenomena for which a subset of training data 112 may be selected.

Still referring to FIG. 3, machine-learning module 200 may be configured to perform a lazy-learning process 316 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 112. Heuristic may include selecting some number of highest-ranking associations and/or training data 112 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail herein.

Alternatively, or additionally, and with continued reference to FIG. 3, machine-learning processes as described in this disclosure may be used to generate machine-learning models 116. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 116 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 116 may be generated by creating an artificial neural network, such as a convolutional neural network comprising an input layer of nodes, one or more intermediate layers, and an output layer of nodes. Connections between nodes may be created via the process of "training" the network, in which elements from a training data 112 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 320.

At least a supervised machine-learning process 320, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include user data 108, as described above as inputs, infectivity parameters 120 as outputs, and a ranking function representing a desired form of relationship to be detected between inputs and outputs; ranking function may, for instance, seek to maximize the probability that a given input and/or combination of elements inputs is associated with a given output to minimize the probability that a given input is not associated with a given output. Ranking function may be expressed as a risk function representing an "expected loss" of an algorithm relating inputs to outputs, where loss is computed as an error function representing a degree to which a prediction generated by the relation is incorrect when compared to a given input-output pair provided in training data 112. Persons skilled in the art, upon reviewing the entirety of this disclosure, will be aware of various possible variations of at least a supervised machine-learning process 320 that may be used to determine relation between inputs and outputs. Supervised machine-learning processes may include classification algorithms as defined above.

Further referring to FIG. 3, machine learning processes may include at least an unsupervised machine-learning processes 324. An unsupervised machine-learning process 324, as used herein, is a process that derives inferences in datasets without regard to labels; as a result, an unsupervised machine-learning process 324 may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 116 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 3, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 112 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 112.

Figure 4:
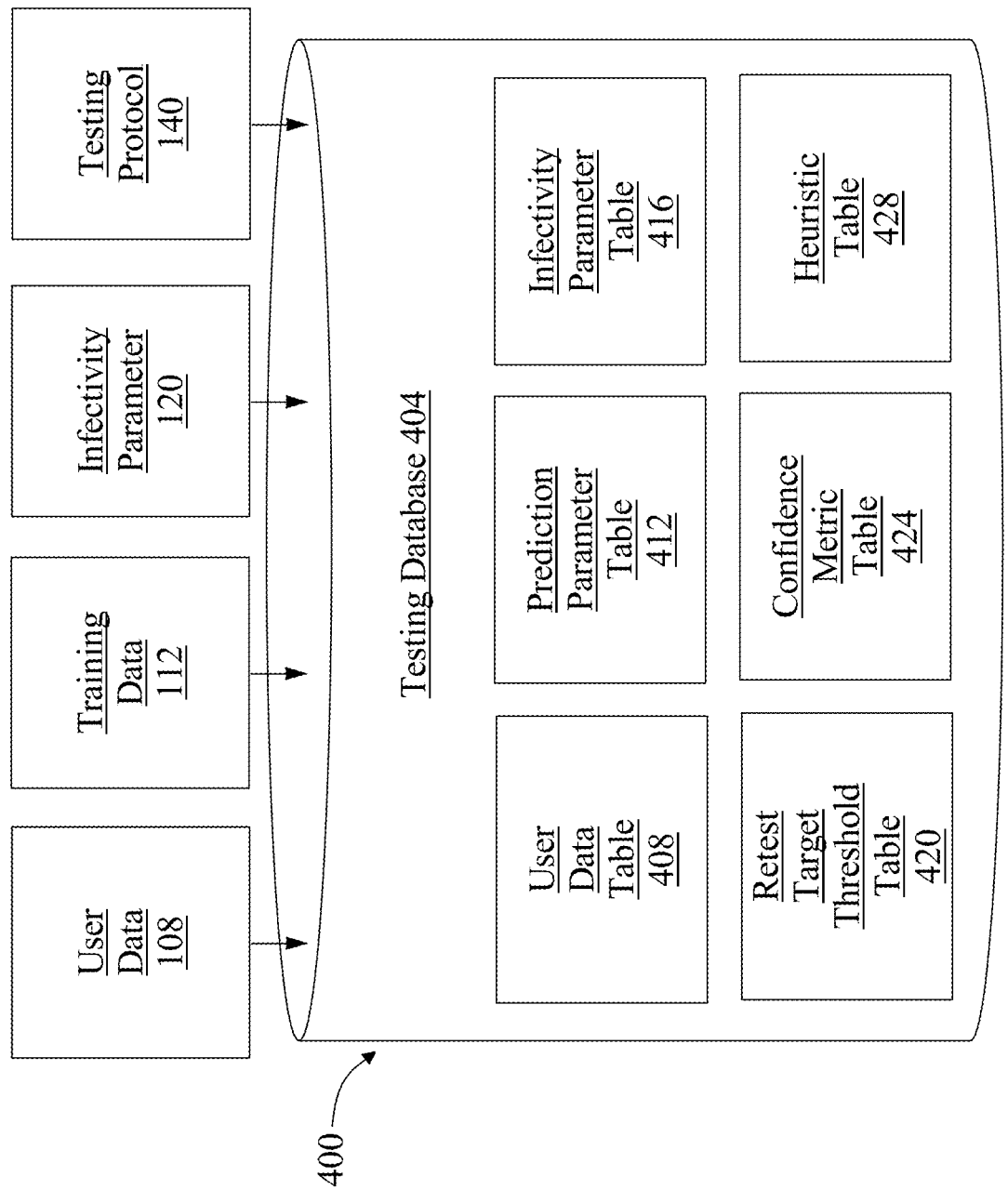
FIG. 4 is a block diagram illustrating an exemplary embodiment of a database.

Referring now to FIG. 4, a non-limiting exemplary embodiment 400 of a testing database 404 is illustrated. Testing database 404 may be implemented, without limitation, as a relational database, a key-value retrieval database such as a NOSQL database, or any other format or structure for use as a database that a person skilled in the art would recognize as suitable upon review of the entirety of this disclosure. Testing database 404 may alternatively or additionally be implemented using a distributed data storage protocol and/or data structure, such as a distributed hash table and the like. Testing database 404 may include a plurality of data entries and/or records, as described above. Data entries in a testing database 404 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure. Computing device 104 may store and/or retrieve any determinations, as described herein, from the testing database 404, such as user data 108, training data 112, infectivity parameters 120, retest target thresholds 136, confidence metrics 144, testing protocols 140, among other input data and determinations made by system 100.

Further referring to FIG. 4, testing database 404 may include, without limitation, and user data table 408, prediction parameter table 412, infectivity parameter 416, retest target threshold table 420, confidence metric table 424, and/or heuristic table 428. Determinations by computing device 104, machine-learning process, machine-learning model, and/or ranking function, may also be stored and/or retrieved from the testing database 404, for instance in non-limiting examples a classifier describing a plurality of training data 112 as it relates to a plurality of prediction parameters, wherein a classifier is an identifier that denotes a subset of data that contains a heuristic and/or relationship, as may be useful to system 100 described herein. As a non-limiting example, testing database 404 may organize data according to one or more instruction tables. One or more testing database 404 tables may be linked to one another by, for instance in a non-limiting example, common column values. For instance, a common column between two tables of testing database 404 may include an identifier of a submission, such as a form entry, textual submission, local access addresses, parameters, rankings, metrics and the like, for instance as defined herein; as a result, a search by a computing device 104 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Still referring to FIG. 4, in a non-limiting embodiment, one or more tables of an testing database 404 may include, as a non-limiting example, an user data table 408, which may include categorized identifying data, as described above, including user parameters includes ages, locations, symptoms, testing results, test types, testing dates, contract tracing data, and the like. One or more tables may include prediction parameter table 412, which may include data regarding mapping user elements to numerical scales for determining infectivity parameters 120, that system 100 may use to retrieve and/or store for determinations herein. One or more tables may include infectivity parameter 416, which may include determinations, variables, relationships, functions, classifiers, data, and the like, for instance and without limitation, that system 100 may use to retrieve and/or store likelihood parameters 124, severity parameters 128, and/or prevalence parameters 132. One or more tables may include retest target threshold table 420, which may include classifiers, numerical values, percentiles, among other metrics, as described above for instance and without limitation, that system 100 may use to retrieve for determining a retest target threshold 136. One of more tables may include a confidence metric table 424, which may include parameters, rankings, outputs, and the like, organized into subsets of data for system 100 to determining testing protocol 140 decisions, retesting procedures, and the like. One or more tables may include, without limitation, a heuristic table 428, which may organize parameters, metrics, rankings, scores, models, outcomes, functions, numerical values, vectors, matrices, and the like, that represent determinations, optimizations, iterations, variables, and the like, include one or more inputs describing potential mathematical relationships, as described herein.

Figure 5:
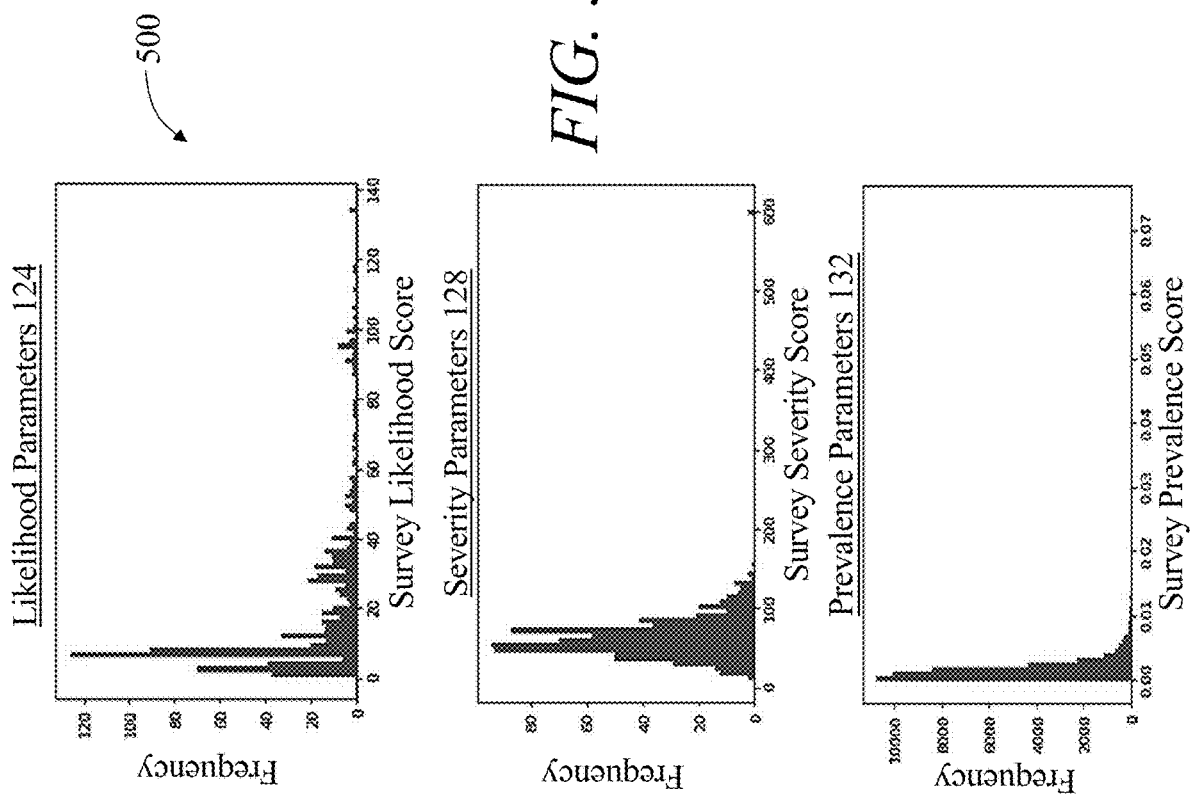
FIG. 5 is a diagrammatic representation illustrating population-based infectivity parameters.

Referring now to FIG. 5, an exemplary embodiment 500 of a distribution of infectivity parameters 120 is illustrated. As described above, a 44-year-old man with 'chills' and 'dry cough with blood' may receive a likelihood parameter 124 score of '57', which may place such a user in the upper half of likelihood parameter 124 scores who have retested positive for COVID-19. Such a likelihood parameter 124 may indicate that a testing protocol 140 that indicates a user be tested. However, the same individual may have a severity score of '77' indicating a severity of COVID-19 closer to the median, perhaps indicating a lower potential for hospitalization. In FIG. 5, the prevalence parameter 132 may be represented as the percent of individuals in a zip code testing positive. In such an example, there are approximately 42,000 zip codes in the United States, and the prevalence of positive cases per capita can be graphed as shown in FIG. 5. As shown in FIG. 5, most zip codes may expect 1-10% of individuals overall testing positive.

Still referring to FIG. 5, likelihood parameter 124 for COVID-19 may include numerical values assigned for symptoms and age ranges according to the trained machine-learning model 116 and training data 112 mapping correlations of age and symptomology to likelihood of having COVID-19 over similar types of infectious disease. For instance, a 44-year-old man with 'chills' and 'dry cough with blood' may receive a likelihood score of '57', as a non-limiting example, using values from a scoring function as illustrated in Table 1 below:

TABLE 1

Likelihood Parameter

| Category | Score |
|---|---|
| "Chills" | 12 |
| "Fatigue" | 25 |
| "General Aches and Pains" | 12 |
| "Dry Cough" | 30 |
| "Cough with Mucus" | 25 |
| "Cough with Blood" | 25 |
| "Shortness of Breath" | 25 |
| "Runny or Stuffy Nose" | 5 |
| "Swollen or Red Eyes" | 5 |
| "Age 0 to 39" | 1 |
| "Age 40 to 49" | 2 |
| "Age 50 to 59" | 6 |
| "Age 60 to 69" | 10 |
| "Age 70 to 79" | 11 |
| "Age 80+" | 12 |

Continuing in reference to FIG. 5, similarly, the severity parameter 128 for COVID-19 may include numerical values assigned for symptoms and age ranges according to the trained machine-learning model 116 and the training data 112 mapping relationships between the manifestation of the disease with underlying co-morbidities. The same user may have experience 'shortness of breath' and has 'high blood pressure,' indicating a severity parameter 128 of '77', as a non-limiting example, using values from a scoring function as illustrated in Table 2 below:

TABLE 2

Severity Parameter

| Category | Score |
|---|---|
| "Fatigue" | 15 |
| "Cough with Mucus" | 16 |
| "Shortness of Breath" | 62 |
| Diarrhea | 25 |
| "Asthma/Lung Condition" | 15 |
| "Heart Conditions" | 25 |
| "High Blood Pressure" | 12 |
| "Type I Diabetes" | 24 |
| "Type II Diabetes" | 24 |
| "Age 0 to 39" | 0 |
| "Age 40 to 49" | 3 |
| "Age 50 to 59" | 9 |
| "Age 60 to 69" | 20 |
| "Age 70 to 79" | 48 |
| "Age 80+" | 114 |

Continuing in reference to FIG. 5, prevalence parameter 132 may include numerical values assigned for rates of infection as a function of location according to the trained machine-learning model 116 and training data 112 mapping correlations of contact tracing and/or case numbers to user location. The prevalence parameter 132 may be calculated for instance as the number of positive cases per capita in each zip code and may be determined for each zip code in the United States, for instance. The prevalence parameter 132 may include a prevalence rate, wherein the number of recovered individuals versus the number of new cases may be considered. As a non-limiting example, using values from a scoring function as illustrated in Table 3 below:

TABLE 3

Prevalence Parameter

| Category | Zip Code | Prevalence Rate |
|---|---|---|
| 0 | 36003 | 0.002739 |
| 1 | 36006 | 0.004430 |
| 2 | 36067 | 0.003161 |
| 3 | 36066 | 0.003161 |
| 4 | 36703 | 0.003036 |
| ... | ... | ... |
| 39262 | 82930 | 0.001285 |
| 39263 | 82937 | 0.001285 |
| 39264 | 82939 | 0.001285 |
| 39265 | 82723 | 0.000866 |
| 39266 | 82715 | 0.000866 |

Figure 6:
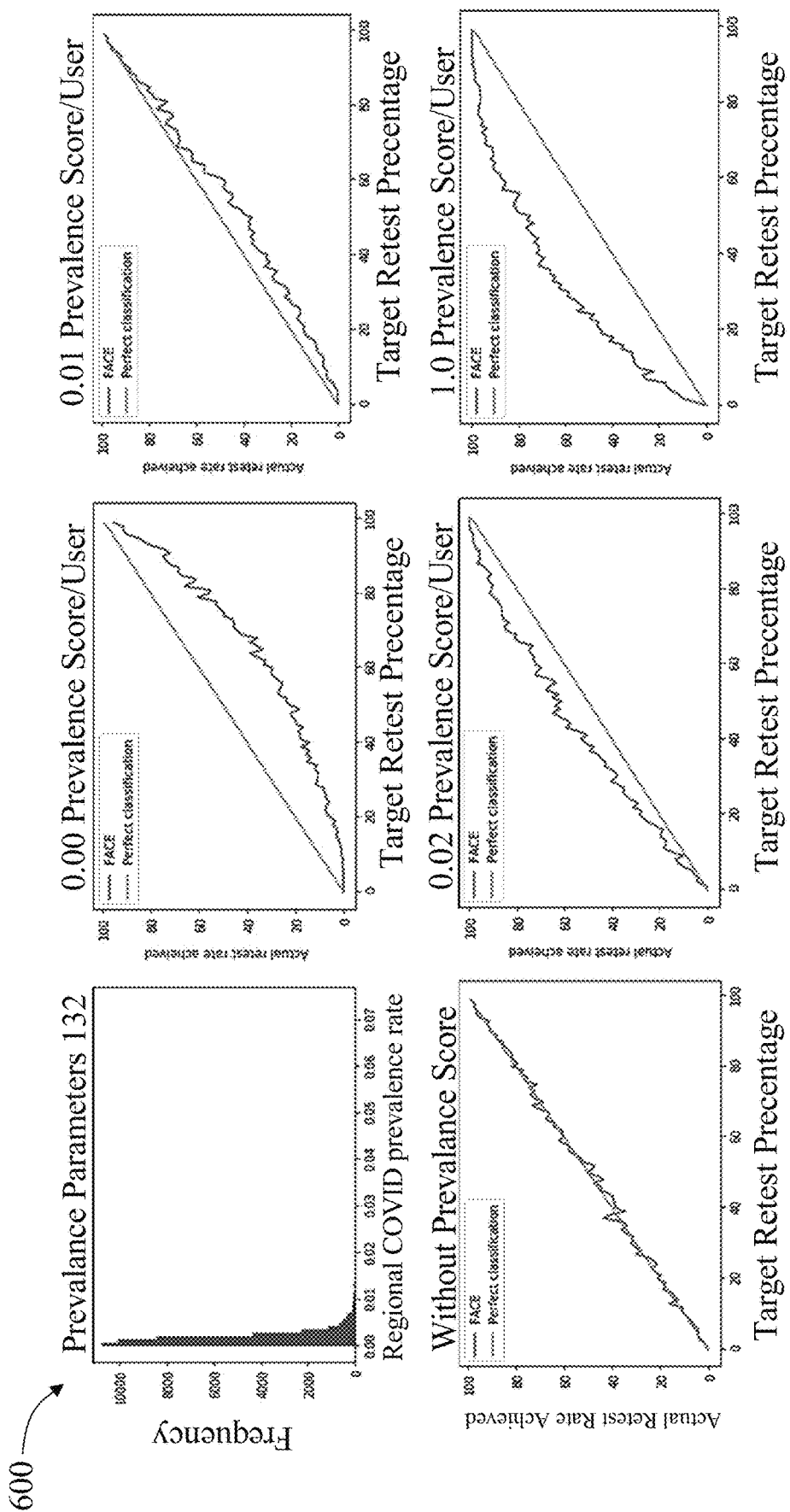
FIG. 6 is a diagrammatic representation demonstrating behavior of prevalence data for calculation of RT-PCR retest eligibility.

Referring now to FIG. 6, an exemplary embodiment 600 of the effect of prevalence parameters 132 on retesting rate is illustrated. The 'actual retest rate" versus a standard 'target retest percentage' of individuals is illustrated at various prevalence parameter 132 values. Without use of the prevalence parameter 132, individuals are tested at the standard target retest percentage set from lack of testing (0%) to universal testing (100%), wherein if 20% of individuals are to be selected to be tested, the algorithm assigned 20% of users a testing protocol 140 that involves COVID-19 testing. At a 0.00 prevalence score, the occurrence of the infectious disease is not detected (or below detection rate) and therefore, the algorithm (FACE) suggests retesting at a much lower rate than retesting each individual who has at least a symptom or co-morbidity, with "perfect classification" indicating the number of individuals tested at each target retest percentage. As prevalence parameter 132 increases to 0.001, or 1% of the population harboring COVID-19, the algorithm suggests a higher rate of testing for individuals showing likelihood parameters 124 an/or severity parameters 128 indicating COVID-19 potentiality. Finally, at 1 prevalence, it is assumed that nearly every individual in a population may have encountered COVID-19, despite low likelihood parameter 124 and/or severity parameter 128. In such a case, the algorithm may suggest a much higher rate of initiating a testing protocol 140 for COVID-19. For instance, as users submit data indicating higher prevalence, the algorithm suggests nearly 100% testing rate as it becomes clear to the machine-learning model that a great number of individuals have COVID-19.

Figure 7:
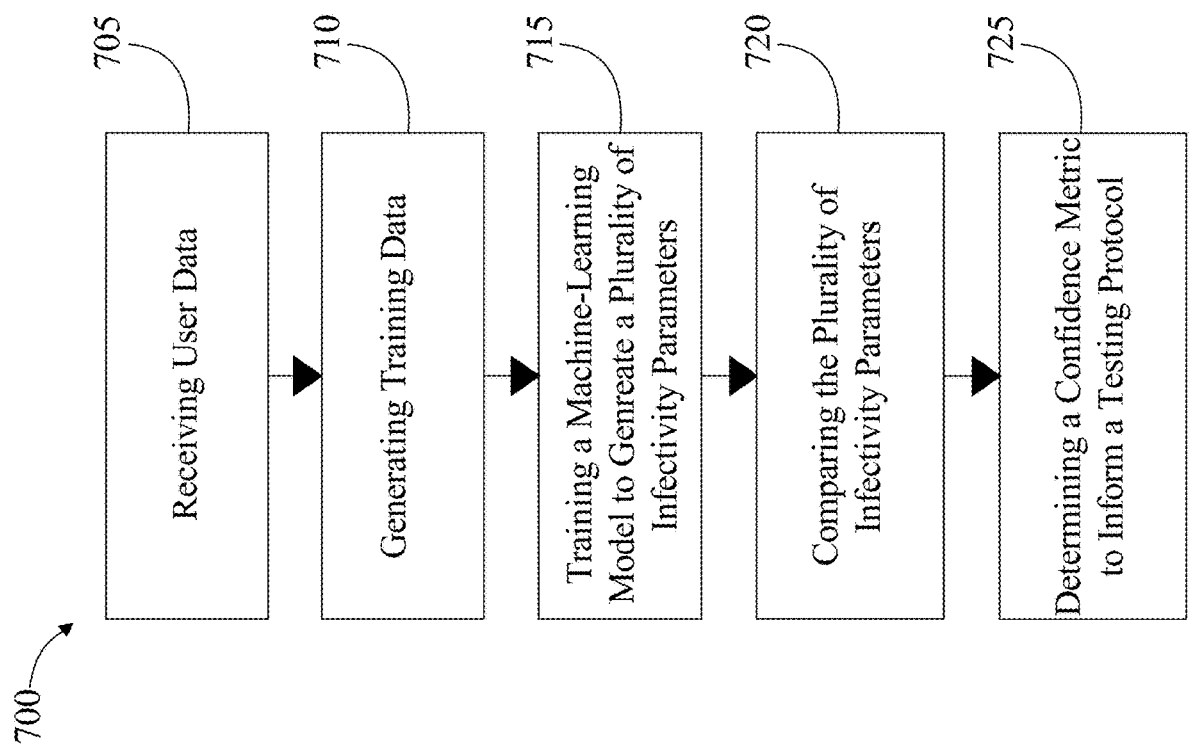
FIG. 7 is a flow diagram of an example of a method for a data driven test result prediction algorithm for infectious disease.

Referring now to FIG. 7, a non-limiting exemplary embodiment of a method 700 for a data driven disease test result prediction is illustrated. At step 705, computing device 104 is configured for receiving user data 108, wherein the user data 108 includes user parameters; this may be implemented, without limitation, as described above in FIGS. 1-7.

Still referring to FIG. 7, at step 710, computing device 104 is configured for generating, using the user data 108, training data 112 wherein the training data 112 includes a plurality of entries wherein each entry correlates user parameter data to at least a prediction parameter of the plurality of prediction parameters associated with an infectious disease. The infectious disease may include 2019-novel Coronavirus acute respiratory disease (COVID-19), the disease caused by Severe Acute Respiratory Syndrome Coronavirus 2 (SARS-CoV-2). Generating training data 112 may include receiving a category of user parameters and generating training data 112 based on the user category; this may be implemented, without limitation, as described above in FIGS. 1-6.

Continuing in reference to FIG. 7, at step 715, computing device 104 is configured for training, using the training data 112 and a machine-learning process, a machine-learning model 116, wherein the trained machine-learning model 116 is configured to generate a plurality of infectivity parameters 120. The plurality of infectivity parameters 120 may include a likelihood parameter 124 that is a quantitative measure of the likelihood that the symptomology data observed for the age of the user is associated with a particular infectious disease. The plurality of infectivity parameters 120 may include a severity parameter 128 that is a quantitative measure of the severity of the particular infectious disease as a function of age and symptomology. The plurality of infectivity parameters 120 may include a prevalence parameter 132 that is determined as a function of the incidence of the disease at the user location. Training the machine-learning model 116 using the machine-learning process may include generating a numerical value scale for the plurality of infectivity parameters 120 as a function of the training data 116, outputting, using the trained machine-learning model 116, the user data 108 input, and the numerical value scale, a quantitative value for each parameter of the plurality of infectivity parameters 120, ranking, using a ranking function, the plurality of infectivity parameters 120, and comparing the plurality of ranked infectivity parameters 120 to the retest target threshold 136; this may be implemented, without limitation, as described above in FIGS. 1-6.

Continuing in reference to FIG. 7, at step 720, computing device 104 is configured for comparing the plurality of infectivity parameters 120 to a retest target threshold 136; this may be implemented, without limitation, as described above in FIGS. 1-6.

Continuing in reference to FIG. 7, at step 725, computing device 104 is configured for determining, as a function of the comparison, a confidence metric 144, wherein the confidence metric 144 informs a testing protocol 140. Determining the confidence metric 144 may include determining a quantitative relationship between the retest target threshold 136 and the plurality of infectivity parameters 120 and generating an output of testability as a function of the testing protocol and the relationship between the rest target threshold and the plurality of infectivity parameters 120. System 100 may include receiving testing protocol data and using the testing protocol data as an input into the machine-learning process, determine, using the trained machine-learning model 116, a testability output corresponding to the testing protocol data; this may be implemented, without limitation, as described above in FIGS. 1-6.

It is to be noted that anyone or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
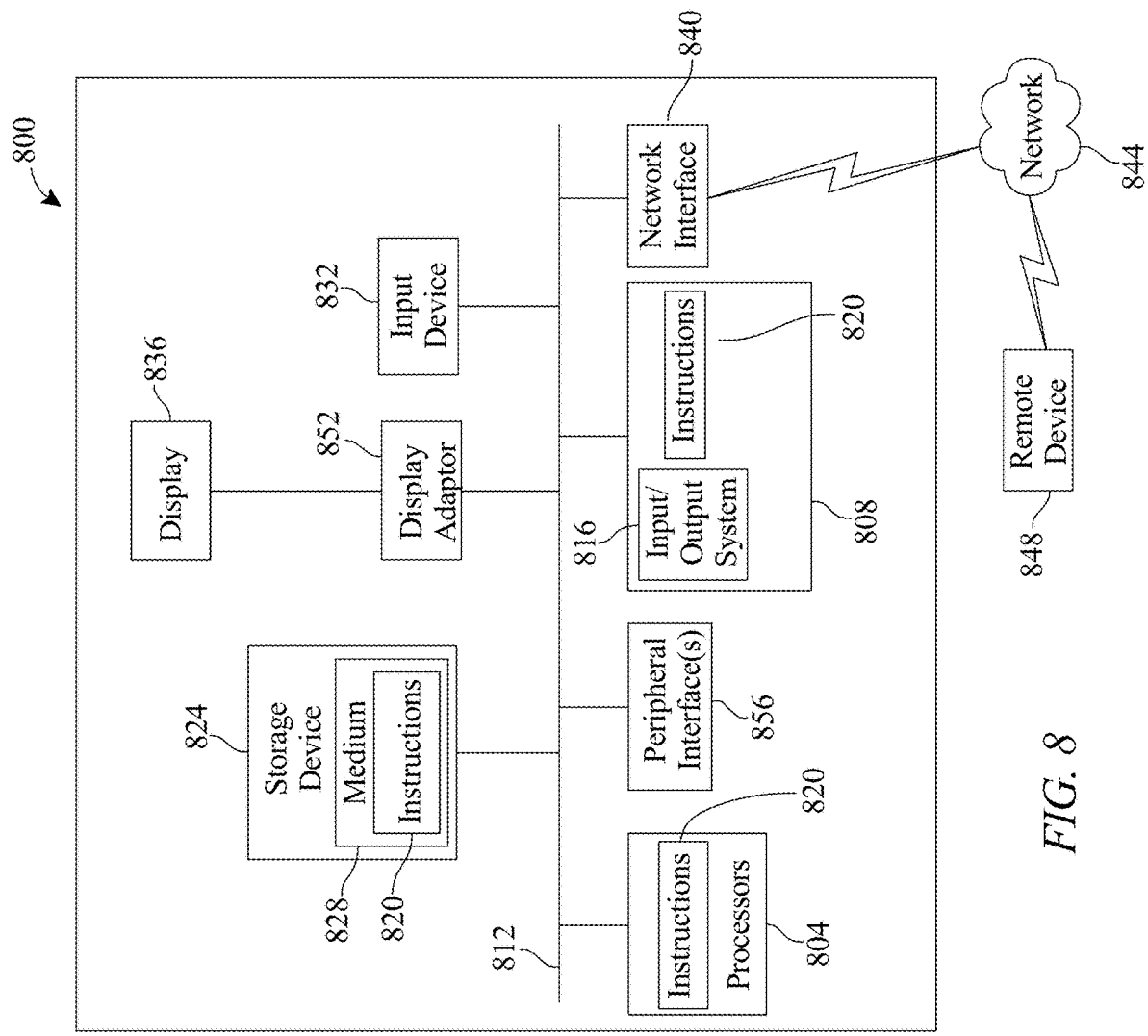
FIG. 8 is a block diagram of a computing system that can be used to implement any one or more of the methods disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for a data driven disease test result prediction, the system comprising:
    a computing device, wherein the computing device is designed and configured to:
    receive user data, wherein the user data includes at least a user parameter;
    generate, as a function of the user data, training data wherein the training data includes a plurality of entries wherein each entry correlates user parameter data to at least a prediction parameter of the plurality of prediction parameters associated with an infectious disease;
    sort the training data using a classification algorithm, wherein the training data is sorted as a function of a COVID-19 status and zip code;
    train, as a function of the training data and a machine-learning process, a machine-learning model wherein the machine-learning model is trained to input the user data and output a plurality of infectivity parameters wherein the plurality of infectivity parameters comprises a likelihood parameter, a severity parameter, and a prevalence parameter;
    calculate, as a function of the at least a user parameter and the trained machine-learning model, the plurality of infectivity parameters;
    compare an aggregation of the plurality of infectivity parameters to a retest target threshold; and
    determine, as a function of the comparison, a confidence metric, wherein the confidence metric informs a testing protocol.

2. The system of claim 1, wherein the infectious disease further comprises a coronavirus.

3. The system of claim 1, wherein generating training data further comprises receiving a parameter category and generating training data as a function of the parameter category.

4. The system of claim 1, wherein the plurality of infectivity parameters includes the likelihood parameter, and wherein comparing the plurality of infectivity parameters to the retest target threshold further comprises comparing as a function of the likelihood parameter.

5. The system of claim 1, wherein the plurality of infectivity parameters includes the severity parameter, and wherein comparing the plurality of infectivity parameters to the retest target threshold further comprises comparing as a function of the severity parameter.

6. The system of claim 1, wherein the plurality of infectivity parameters includes the prevalence parameter, and wherein comparing the plurality of infectivity parameters to the retest target threshold further comprises comparing as a function of the prevalence parameter.

7. The system of claim 1, wherein training the machine-learning model using the machine-learning process further comprises ranking, using a ranking function, the plurality of infectivity parameters so that the aggregation of the plurality of infectivity parameters are directly comparable to the retest target threshold.

8. The system of claim 1, wherein determining the retest target threshold further comprises using a trained machine-learning model and a numerical value scale for the prevalence parameter.

9. The system of claim 1, wherein determining the confidence metric further comprises:
    determining a quantification of a relationship between the retest target threshold and the plurality of infectivity parameters; and
    generating an output to retest a user as a function of the testing protocol and the relationship between the rest target threshold and the plurality of infectivity parameters.

10. The system of claim 1, further comprising:
    receiving user testing protocol data; and
    selecting a testing protocol as a function of the confidence metric based on the user testing protocol data.

11. A method for a data driven disease test result prediction, the method comprising:
    receiving, by a computing device, user data, wherein the user data includes at least a user parameter;
    generating, by the computing device, as a function of the user data, training data wherein the training data includes a plurality of entries wherein each entry correlates user parameter data to at least a prediction parameter of the plurality of prediction parameters associated with an infectious disease;
    sorting, by the computing device, the training data using a classification algorithm, wherein the training data is sorted as a function of a COVID-19 status and zip code;
    training, by the computing device, as a function of the training data and a machine-learning process, a machine-learning model wherein the machine-learning model is trained to input the user data and output a plurality of infectivity parameters wherein the plurality of infectivity parameters comprises a likelihood parameter, a severity parameter, and a prevalence parameter;
    calculating, by the computing device, as a function of the at least a user parameter and the trained machine-learning model, the plurality of infectivity parameters;
    comparing, by the computing device, an aggregation of the plurality of infectivity parameters to a retest target threshold; and
    determining, by the computing device, as a function of the comparison, a confidence metric, wherein the confidence metric informs a testing protocol.

12. The method of claim 11, wherein the infectious disease further comprises a coronavirus.

13. The method of claim 11, wherein generating training data further comprises receiving a parameter category and generating training data as a function of the parameter category.

14. The method of claim 11, wherein the plurality of infectivity parameters includes the likelihood parameter, and wherein comparing the plurality of infectivity parameters to the retest target threshold further comprises comparing as a function of the likelihood parameter.

15. The method of claim 11, wherein the plurality of infectivity parameters includes the severity parameter, and wherein comparing the plurality of infectivity parameters to the retest target threshold further comprises comparing as a function of the severity parameter.

16. The method of claim 11, wherein the plurality of infectivity parameters includes the prevalence parameter, and wherein comparing the plurality of infectivity parameters to the retest target threshold further comprises comparing as a function of the prevalence parameter.

17. The method of claim 11, wherein training the machine-learning model using the machine-learning process further comprises ranking, using a ranking function, the plurality of infectivity parameters so that the aggregation of the plurality of infectivity parameters are directly comparable to the retest target threshold.

18. The method of claim 11, wherein determining the retest target threshold further comprises using a trained machine-learning model and a numerical value scale for the prevalence parameter.

19. The method of claim 11, wherein determining the confidence metric further comprises:
  determining a quantification of a relationship between the retest target threshold and the plurality of infectivity parameters; and
  generating an output to retest a user as a function of the testing protocol and the relationship between the rest target threshold and the plurality of infectivity parameters.

20. The method of claim 11, further comprising:
  receiving user testing protocol data; and
  selecting a testing protocol as a function of the confidence metric based on the user testing protocol data.

* * * * *